United States Patent [19]

Nedelec et al.

[11] Patent Number: 4,661,482
[45] Date of Patent: Apr. 28, 1987

[54] USE OF PYRAZOLOBENZOXAZINES IN METHOD OF TREATING CEREBRAL SENESCENCE AND CEREBRAL HYPOXIN

[75] Inventors: Lucien Nedelec, Le Raincy; Patrick Fauveau, Livry Gargan; Gilles Hamon, Montrouge; Claude Oberlander, Paris, all of France

[73] Assignee: Roussel Uclaf, Paris, France

[21] Appl. No.: 833,347

[22] Filed: Feb. 25, 1986

[30] Foreign Application Priority Data

Mar. 1, 1985 [FR] France .................. 85 03036

[51] Int. Cl.$^4$ .................. A61K 31/535; C07D 265/34
[52] U.S. Cl. .................. 514/227; 514/232; 514/237; 514/239; 544/101; 544/105
[58] Field of Search .............. 544/101; 514/232, 227, 514/237, 239

[56] References Cited

U.S. PATENT DOCUMENTS 4,552,956  11/1985  Booher et al. .................. 544/101

Primary Examiner—Richard L. Raymond
Attorney, Agent, or Firm—Bierman & Muserlian

[57] ABSTRACT

Novel pyrazolobenzoxazines of the formula

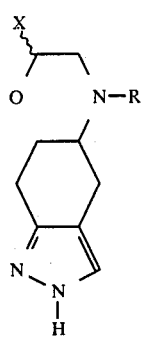

I wherein R is selected from the group consisting of hydrogen, alkyl of 1 to 5 carbon atoms, cycloalkylalkyl or 4 to 7 carbon atoms, alkenyl and alkynyl of 3 to 5 carbon atoms with the proviso that the multiple bond is not between the carbon $\alpha$- and $\beta$- to the nitrogen atom, aralkyl of 7 to 12 carbon atoms and aralkyl of 7 to 12 carbon atoms substituted with at least one member of the group consisting of alkyl and alkoxy of 1 to 5 carbon atoms, amino, -OH and halogen, X is selected from the group consisting of hydrogen and —CH$_2$—S—Alk, Alk is alkyl of 1 to 5 carbon atoms, the wavy line indicates the $\alpha$- or $\beta$-position and their non-toxic, pharmaceutically acceptable acid addition salts having dopaminergic agonistic, hypotensive, antihypertensive and antianoxic properties and their preparation.

6 Claims, No Drawings

USE OF PYRAZOLOBENZOXAZINES IN METHOD OF TREATING CEREBRAL SENESCENCE AND CEREBRAL HYPOXIN

OBJECTS OF THE INVENTION

It is an object of the invention to provide the novel compounds of formula I and their non-toxic, pharmaceutically acceptable acid addition salts and a process for their preparation.

It is another object of the invention to provide novel hypotensive and antianoxic and dopaminergic agonistic compositions and novel methods of inducing hypotensive, antihypertensive, antianoxic and dopaminergic agonistic activity in warm-blooded animals.

These and other objects and advantages of the invention will become obvious from the following detailed description.

THE INVENTION

The novel compounds of the invention are selected from the group consisting of pyrazolobenzoxiazines of the formula

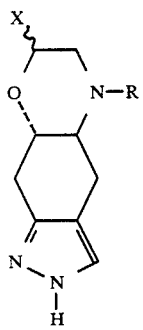

wherein R is selected from the group consisting of hydrogen, alkyl of 1 to 5 carbon atoms, cycloalkylalkyl of 4 to 7 carbon atoms, alkenyl and alkynyl of 3 to 5 carbon atoms with the proviso that the multiple bond is not between the carbon α- and β- to the nitrogen atom, aralkyl of 7 to 12 carbon atoms and aralkyl of 7 to 12 carbon atoms substituted with at least one member of the group consisting of alkyl and alkoxy of 1 to 5 carbon atoms, amino, —OH and halogen, X is selected from the group consisting of hydrogen and —CH₂—S—Alk, Alk is alkyl of 1 to 5 carbon atoms, the wavy line indicates the α- or β-position and their non-toxic, pharmaceutically acceptable acid addition salts.

Exammples of alkyl and alkoxy of 1 to 5 carbon atoms are methyl, ethyl, n-propyl, isopropyl, methoxy, ethoxy, n-propoxy and isopropoxy and cycloalkylalkyl of 4 to 7 carbon atoms may be cyclopropylmethyl or cyclobutylmethyl. Examples of arylalkyl of 7 to 12 carbon atoms are benzyl, phenethyl and naphthylmethyl which can be substituted with one or more substituents. Suitable halogens include bromine and chlorine. The dotted line indicates the trans form.

Examples of suitable acids for the formation of the non-toxic, pharmaceutically acceptable acid addition salts are mineral acids such as hydrochloric acid, hydrobromic acid, nitric acid, sulfuric acid or phosphoric acid and organic acids such as formic acid, acetic acid, propionic acid, benzoic acid, maleic acid, fumaric acid, succinic acid, tartaric acid, citric acid, oxalic acid, glyoxalic acid, aspartic acid, alkane sulfonic acids such as methane sulfonic acid or ethane sulfonic acid, aryl sulfonic acids such as p-toluene sulfonic acid or benzene sulfonic acid or arylcarboxylic acids.

Among the preferred compounds of formula I are those wherein X is hydrogen, those wherein X is —CH₂—S—Alk and particularly in the α-position, those wherein R is hydrogen or alkyl of 1 to 5 carbon atoms and their non-toxic, pharmaceutically acceptable acid addition salts. Especially preferred are [4a SR trans]-5-propyl-2,4,4a,5,6,7,8a,9-octahydropyrazolo-[4,3-g]-1,4-benzoxazine and [4a SR trans] 5-methyl-2,4,4a,5,6,7,,8a,9-octahydropyrazolo[4,3-g]-1,4-benzoxazine and their non-toxic, pharmaceutically acceptable acid addition salts.

The novel process of the invention for the preparation of the compounds of formula I wherein X is hydrogen comprises reacting a ketone enolate of the formula

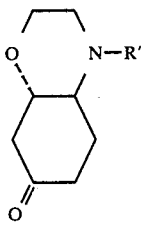

wherein R' is R other than hydrogen with an alkyl formate of the formula $$HCOO-Alk \qquad III$$

wherein Alk is alkyl of 1 to 4 carbon atoms to form a compound of the formula

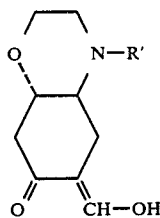

reacting the latter with hydrazine to obtain a compound of the formula $I_A$:

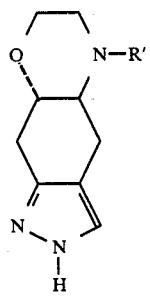

which may be isolated, and if desired, salified, or, when R' is benzyl, subjecting the same to catalytic hydrogenation to obtain a product of the the formula

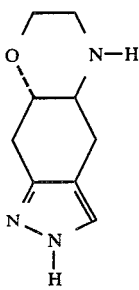

which may be isolated, and if desired, salified or is reacted with a halide of the formula Hal-R''   V wherein Hal is chlorine, bromine or iodine, and R'' has the significance of R except hydrogen or methyl to obtain a product of the formula

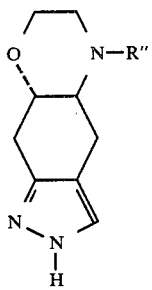

I$_C$ which may be isolated and if desired, salified.

The formation of the enolate of the ketone of formula II is preferably carried out in the presence of an alkali metal hydride such as sodium hydride or an alkali metal alcoholate such as sodium ethylate or potassium tertbutylate, particularly in the presence of a catalytic quantity of an aliphatic alcohol such as methanol or ethanol. The alkyl formate may be for example, methyl or propyl formate, and preferably ethyl formate. Hydrazine is preferably used in the form of hydrazine hydrate. The catalytic hydrogenation is carried out, for example, in the presence of a catalyst such as nickel or preferably palladium. The reaction of the compound of formula I$_B$ with the halide of formula V is preferably carried out in the presence of a base such as an alkali metal carbonate or bicarbonate such as sodium carbonate, alkali metal hydroxide such as sodium or potassium hydroxide, an alkali metal alcoholate such as sodium ethylate or a tertiary amine such as triethylamine or pyridine. The halide of formula V is for example, a bromide or chloride, and preferably an iodide.

In a variant or of the process of the invention, the ketone of formula II is reacted with dimethylformamide dimethylacetal at reflux of a solvent with a boiling point of 80° to 130° C., then treated with hydrazine to obtain a product of formul I$_A$ which, if desired, is treated as indicated above. The solvent with a boiling point of 80° to 130° C. is, for example, benzene, toluene or xylene.

To prepare the compounds of formula I wherein R is other than hydrogen, a compound of formula I$_B$ is reacted with a derivative of the formula

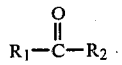

XIV wherein R$_1$—CH—R$_2$ is R other than hydrogen in the presence of a reducing agent like alkali metal borohydride such as sodium borohydride or an alkali metal cyanoborohydride such as sodium cyanoborohydride or catalytic hydrogenation, for example, If formaldehyde or acetaldehyde are used, R is methyl or ethyl, respectively.

The products of formula II can be prepared by reacting a compound of the formula

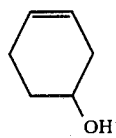

VI to protect the hydroxyl to obtain a compound of the formula

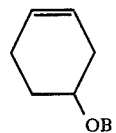

VII wherein B is a protector group, reacting the latter with a peracid to obtain a compound of the formula

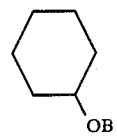

VIII wherein the wavy lines indicate that the conformation is syn or anti, reacting the anti isomer with an amine of the formula

R'—NH$_2$   IX wherein R' has the above definition to obtain the isomers of the formulae

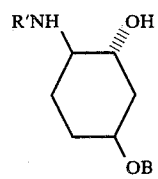

X$_a$

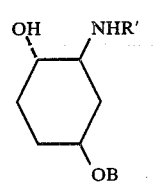

X$_b$ reacting isomer Xa with an ethyl hydroxy halide to obtain a compound of the formula

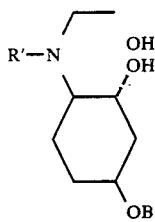

cyclizing the latter to obtain a compound of the formula

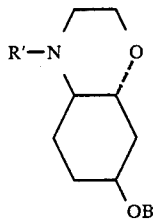

submitting the latter to the action of a deblocking agent of the hydroxyl to obtain a compound of the formula

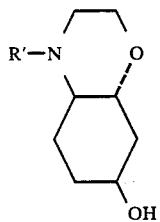

an oxidizing the latter as to obtain the corresponding compound of formula II.

The standard protector group of the hydroxyl function is, for example, a silyl residue such as dimethyl tert-butylsilyl, trimethylsilyl or diphenylmethylsilyl, or an ester such as a benzoate. The operation is preferably done with a corresponding silyl halide in the presence of 4-dimethylamino-pyridine in the case of a silyl ether or with a benzoyl in the presence of a condensation agent such as described above in the case of a benzoyl radical.

The peracid used, for example, is peracetic acid or pertrifluoroacetic acid and, preferably, m-chloro-perbenzoic acid. The operation is preferably done in the presence of a base such as an alkali metal carbonate. The reaction of the epoxide of formula VIII with an amine of formula IX is preferably carried out at reflux of an alkanol such as methanol or ethanol.

The hydroxyethyl halide is, for example, a chloride or bromide, and preferably an iodide and it is advantageously reacted in the presence of an alkali metal carbonate or a tertiary amine. The cyclization of the product of formula XI is preferably carried out by the activation of the primary hydroxyl, for example with N-chlorodiisopropylamine-Tris dimethylamino phospine complex at a low temperature of about −40° C.

The deblocking of the hydroxyl is carried out under usual conditions depending upon the specific blockage agent. Examples are the action of tetrabutylammonium or the reflux of a solvent such as benzene, toluene or xylene in the presence of an acid such as p-toluene sulfonic acid, sulfonic acid or even the action of an acetic acid-tetrahydrofuran-water mixture in the case of a silyl ether. In the case of the benzoate, the reaction is effected with a base such as an alkali metal hydroxide like sodium or potassium hydroxide. The oxidation of the compound of formula XIII is carried out for example, with pyridine dichromate, pyridine chlorochromate, or preferably with a chromic anhydride-sulfuric acid-water mixture (Heibron-Jones reagent).

The process for the preparation of compounds of formula I where X is —$CH_2$—S—Alk comprises reacting a ketone of the formula

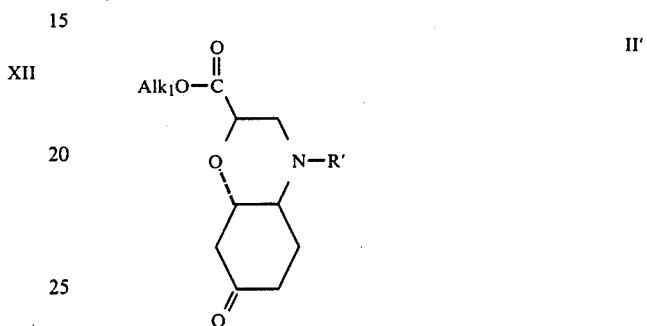

wherein R′ has the above definition and $Alk_1$ is alkyl of 1 to 4 carbon atoms with the dimethylacetal of dimethylformamide, then with hydrazine and finally with an alcoholysis agent to obtain a compound of the formula

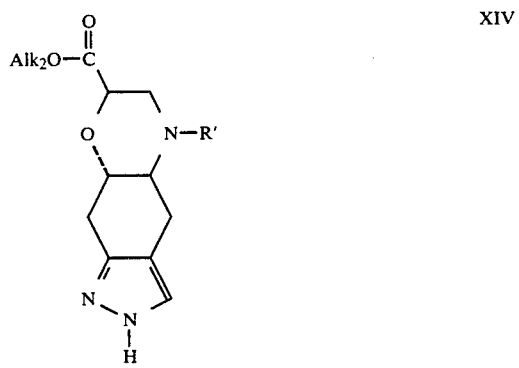

wherein $Alk_2$ is alkyl of 1 to 4 carbon atoms and if R′ is benzyl, subjecting the latter to catalytic hydrogenation to obtain a compound of the formula

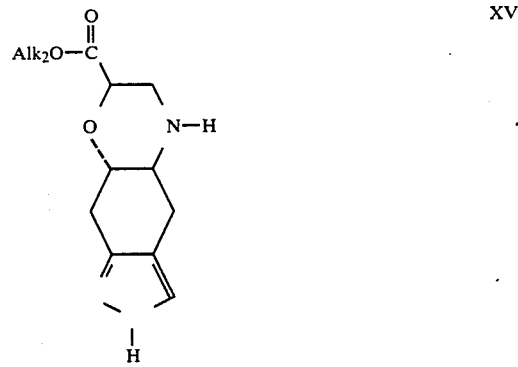

reacting the latter with a halide of the formula

Hal—R"  V wherein R" and Hal have the above definitions to obtain a compound of the formula

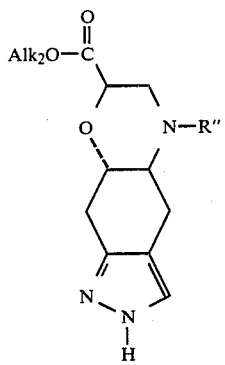   XVI reacting a compound of formulae XIV, XV or XVI with a reducing agent to obtain a compound of the formula

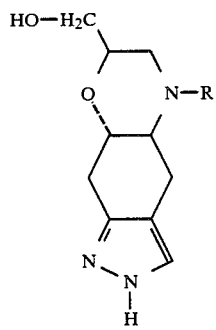   XVII reacting the latter with methane chloride or p-toluene sulfonyl chloride to obtain a compound of the formula

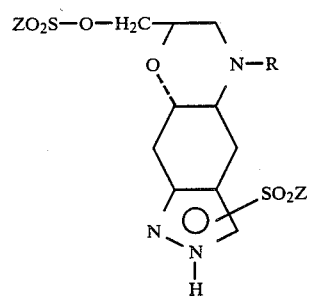   XVIII wherein R has the above definition and Z is —CH$_3$ or p-tolyl and reacting the latter with an alkyl mercaptan to obtain a compound of the formula

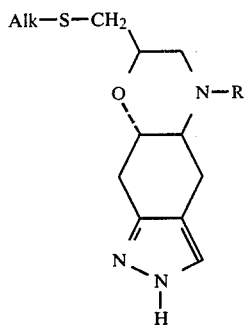   I$_D$ which may be isolated and optionally salified.

The reaction of the ketone of formula II' with dimethylformamide dimethylacetal then with hydrazine is carried out preferably in conditions indicated previously. The reaction with hydrazine can lead to the formation of a hydrazide by reaction with the ester function and the latter is regenerated by alcoholysis in the presence of an acid resin or a copper salt, preferably cuprous chloride with an alkanol of the formula Alk$_2$—OH, Alk$_2$ having the above definition. The catalytic hydrogenation of the compound of formula XIV and the reaction with the halide of formula V are carried out preferably in the conditions described previously.

To introduce into a compound of formula XV a group where R is other than hydrogen and especially methyl, the compound is reacted with a compound of the formula

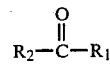

in the presence of a reducing agent. The reduction of the compounds of formulae XIV, XV or XVI is preferably effected with sodium borohydride at reflux of a solvent such as dioxane, dioxane-methanol or dioxane-ethanol. Other reducing agents such as aluminum lithiumhydride or sodium cyanoborohydride can also be used.

The reaction of the compound of formula XVIII with an alkylmercaptan is preferably carried out in the presence of am alkali metal hydride such as sodium hydride in a solvent such as dimethylacetamide and the alkylmercaptan is preferably methylmercaptan. The action of methane chloride or p-toluene sulfonyl chloride on the compound of formula XVII leads to a product substituted also on the pyrazole nucleus which substitution is eliminated by the action of the alkylmercaptan in the presence of sodium hydride.

The

residue in the compound of formula II' can be in the α or β-position and the process of the invention leads to one or other of the isomers with the formula I or to their mixture depending upon the starting product used. The separation of the isomers α and β can, if desired be carried out at any one of the stages of the process.

The compounds of formula II' can be prepared by reacting a compound of formula Xa with alkyl glycidate of the formula

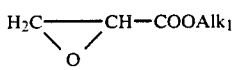   XIX wherein Alk₁ has the above definition to obtain a compound of the formula

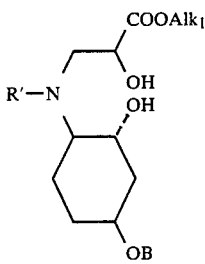   XI' wherein R', B and Alk₁ have the above definition cyclizing the latter to obtain a compound of the formula

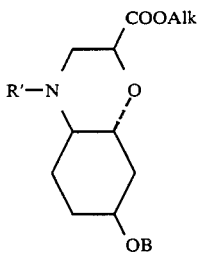   XII' optionally separating the isomers at position 2, reacting the isomer or mixture of isomers with a deblocking agent of the hydroxyl function to obtain a compound of the formula

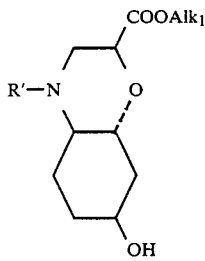   XIII' in the form of one or other of the isomers at position 2 or their mixture and reacting the latter with an oxidizing agent to obtain the corresponding compound of formula II', in the form of one or other of the isomers at position 2, or their mixture, which, if desired, is separated.

The alkyl glycidate is preferably ethyl glycidate and the operation is done at reflux of an alkanol which is preferably ethanol. The cyclization of the compound of formula XI', the deblocking of the hydroxyl and the oxidation of the compound of formula XIII' can be carried out under the conditions described previously for preparation of the compound of formula II. The oxidation of the compounds of formula XIII' can also be carried out by Corey's method, that is by N-chlorosuccinimide in the presence of dimethyl sulfide.

The separation of the isomers can be carried out at any stage by the usual methods, particularly by chromatography.

The derivatives of formula I present a basic character and the addition salts of the compounds of formula I can advantageously be prepared by reaction with a mineral or organic acid with the said compound of formula I in substantially stoichiometrical proportions. The salts can be prepared without isolating the corresponding bases.

The dopaminergic agonistic, hypotensive, antihypertensive and antianoxic compositions of the invention are comprised of an effective amount of at least one compound of formula I and their non-toxic, pharmaceutically acceptable acid addition salts and an inert pharmaceutical carrier or excipient. The compositions may be in the form of tablets, dragees, capsules, granules, suppositories and injectable solutions or suspensions.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

The compositions are useful for the treatment of neurological syndromes of extrapyramidal origin, for example in the treatment of Parkinson's disease and in the treatment of post-encephalitic parkinsonian syndromes and are also useful in the treatment of essential arterial hypertension, hypertension of the fifties, menopause, diabetes, obesity and plethoria, as well as the treatment of arterial hypertension of the elderly, or those attacked by arteriosclerosis, and in the treatment of hypertension of renal origin. They can also be used in the treatment of cerebral senescence or manifestations linked to a cerebral hypoxia.

Among the preferred compositions of the invention are those wherein X is hydrogen, those wherein X is —CH₂—S—Alk and particularly in the α-position, those wherein R is hydrogen or alkyl of 1 to 5 carbon atoms and their non-toxic, pharmaceutically acceptable acid addition salts. Especially preferred are [4a SR trans]-5-propyl-2,4,4a,5,6,7,8a,9-octahydropyrazole-[4,3-g]-1,4-benzoxazine and their non-toxic, pharmaceutically acceptable acid addition salts.

The novel method of the invention for inducing dopaminergic agonistic, hypotensive, antihypertensive and antianoxic activity in warm-blooded animals, including humans, comprises administering to warm-blodded animals an effective amount of at least one compound of formula I and their non-toxic, pharmaceutically acceptable acid addition salts. The compounds can be administered orally, rectally or parenterally and the usual daily dose is 0.015 to 2.75 mg/kg depending on the specific compound, the method of administration and the condition treated. For example, the compound of Example 3 is administered orally to adult humans at a dose of 0.015 to 1.5 mg/kg for treatment or cerebral senescence.

The compounds of formula IV are novel intermediates and are an object of the invention.

In the following examples there are described several preferred embodiments to illustrate the invention. However, it should be understood that the invention is not intended to be limited to the specific embodiments.

EXAMPLE 1

[4a-SR-trans]-2,4,4a,5,6,7,8a,9-octahydrobenzyl-pyrazolo[4,3-g]-1,4-benzoxazine

STEP A: (3-cyclohexen-1-oxy)-dimethyl-(1,1-dimethylethyl)-silane

A solution of 10 g of 3-cyclohexen-1-ol in 100 ml of methylene chloride was stirred under an inert atmosphere with 12 g of 4-dimethylaminopyridine and 17 ml of triethylamine and then over 1 hour, 15 g of silyl dimethyl tert-.butyl chloride were added dropwise. The mixture was stirred for 1 hour and after filtering, washing the filtrate with 2N hydrochloride acid, then with water, drying and evaporating to dryness under reduced pressure, then chromatographing over silica and eluting with cyclohexane-ethyl acetate (7-3), 19.5 g of (3-cyclohexen-1-oxy)-dimethyl-(1,1-dimethylethyl)-silane were obtained.

STEP B: Dimethyl-(1,1-dimethylethyl)-[1 SR (1α, 3β, 6α)-7-oxabicyclo-[4,1,0]-heptan-3-oxy]-silane.

17 g of the product of Step A and 10.2 g of sodium carbonate in 200 ml of methylene chloride were stirred under an inert atmosphere and cooled to 0°-+5° C. A solution of 20.6 g of m-chloroperbenzoic acid in 200 ml of methylene chloride was added dropwise to the mixture which was then stirred at 5° C. for 16 hours. The precipitate formed was recovered by filtration and was washed with methylene chloride. The filtrate was washed with a solution of sodium thiosulfate, dried and evaporated to dryness under reduced pressure. After purifying the residue by chromatography over silica, the first eluted fraction (eluent:benzene) corresponding to the epoxy of the desired anti compound was collected to obtain 5.8 g of dimethyl-(1,1-dimethylethyl)-[1 SR (1α, 3β, 6α)-7-oxabicyclo-[4,1,0]-heptan-3-yl-oxy]-silane.

STEP C: Dimethyl (1,1-dimethylethyl) [1 RS (1α, 3β, 4')-3-hydroxy-4-[benzylamino]-cyclohexyloxy]-silane A mixture of 7.3 g of the product of Step B in 70 ml of methanol and 16 ml of benzylamine was refluxed for 16 hours with stirring under an inert atmosphere. After evaporating to dryness under reduced pressure and purifying by chromatography over silica (eluent:benzene-ethyl acetate 5-5), 4 g of dimethyl (1,1-dimethylethyl) [1 RS (1α, 3β, 4α)-3-hydroxy-4-[benzylamino]-cyclohexyloxy]-silane were obtained corresponding to the most mobile fraction. It melted at ≈65° C. after crystallization from hexane.

STEP D: Dimethyl (1,1-dimethylethyl) [1 SR (1α, 3β, 4α)-3-hydroxy-4-[(2-hydroxyethyl)-benzylamino]-1-cyclohexyloxy]-silane A mixture of 16 g of the product of Step C in 100 ml of dimethylformamide and 13.1 g of potassium carbonate and 28 ml of bromoethanol was stirred for 16 hours at 70° C. under an inert atmosphere. After pouring into ice, extracting several times with methylene chloride, washing with water, drying, evaporating to dryness under reduced pressure, and purifying by chromatography over silica (eluent:benzene-ethyl acetate 5-5), 14.8 g of dimethyl (1,1-dimethylethyl) [1 SR (1α, 3β, 4α)-3-hydroxy-4-[(2-hydroxyethyl)-benzylamino]-1-cyclohexyloxy]-silane melting at ≈88° C. after crystallization from hexane were obtained.

STEP E: Dimethyl (1,1-dimethylethyl)-[4a SR (4aα, 7β, 8aβ)-octahydro-2H-1,4-benzoxazin-7-yloxy]-silane 18.6 ml of tris dimethylaminophosphine were added dropwise under an inert atmosphere at about −40° C. to 14.4 g of the product of Step D in 250 ml of methylene chloride and 12.8 g of N-chlorodiisopropylamine. After allowing the temperature to return to ambient, adding water, extracting several times with methylene chloride, drying, evaporating to dryness under reduced pressure, and purifying by chromatography over silica (eluent:benzene-ethyl acetate 9-1), 12.3 g of dimethyl (1,1-dimethylethyl)-[4a SR (4aα, 7β, 8aβ)-octahydro-2H-1,4-benzoxazin-7-yloxyl]-silane were obtained.

STEP F: [4a αSR (4aα, 7β, 8aβ)-octahydro-4-benzyl-2H-1,4-benzoxazin-7-ol

A mixture of 11.9 g of the product of Step E in 100 ml of tetrahydrofuran and 66 ml of a molar solution of ammonium tetrabutyl fluoride in tetrahydrofuran was stirred for 16 hours under an inert atmosphere. Ater pouring into water, extracting several times with methylene chloride, evaporating to dryness under reduced pressure, and purifying by chromatography on silica (eluent:methylene chloride-methanol 95-5), 6.2 g of [4a SR (4aα, 7β, 8aβ)]-octahydro-4-benzyl-2H-1,4-benzoxazine-7-ol were obtained.

STEP G: [4a SR trans]-octahydro-4-benzyl-7H-1,4-benzoxazine-7-one 12 ml of Heilbron-Jones reagent (270 g of chromic anhydride, 230 ml of concentrated sulfuric acid, water to make up to 1 liter) were added dropwise with stirring at 0° C. to a solution of 6 g of the product of Step F in 60 ml of acetone, and the mixture was stirred for 90 minutes. After adding ice, cooling to 0° C., alkalinizing with 2N aqueous sodium hydroxide solution, extracting several times with methylene chloride, washing with water, drying, evaporating to dryness under reduced pressure, and purifying by chromatography over silica (eluent: methylene chloride-methanol 95-5), 4.14 g of [4a SR trans]-octahydro-4-benzyl-2H-1,4-benzoxazine-7-one were obtained in the form of a colorless oil.

STEP H: [4a SR trans]-6-hydroxy-methylene-octahydro-4-benzyl-7H-1,4-benzoxazin-7-one A mixture of 1.42 g of 50% sodium hydride in 50 ml of ether was stirred under an inert atmosphere with 4.6 ml of ethyl formate and 0.2 ml of ethanol and then a solution of 3.5 g of [4a SR trans]-octahydro-4-benzyl-7H-1,4-benoxazin-7-one in 40 ml of ether was added dropwise over 30 minutes. After standing for 90 minutes with stirring, ice was added and the mixture was acidified with an aqueous 2N hydrochloric acid solution. The decanted aqueous phase was brought to a pH of 5 with an aqueous 2N sodium hydroxide solution. After extracting with methylene chloride, washing with water, drying and evaporating to dryness under reduced pressure, 3.6 g of a residue was obtained which was purified by chromatography over silica. Elution with benzene-ethyl acetate (7-3) yielded 2.7 g of [4a SR trans]-6-hydroxy-methylene-octahydro-4-benzyl-7H-1,4-benzoxazin-7-one in the form of a yellow oil.

UV Spectrum (ethanol): for M.W.=273.31. Max. 278 nm, $E_1^1$=298=8,100; Inflexion: 311 nm, $E_1^1$=111; Inflexion: 342 nm, $E_1^1$=29;

NMR Spectrum in CDCl₃ at 250 MHz. peak at 14.3 ppm (H of hydroxy); 8.70 ppm (H of 6=CH); peaks at 2.45 and 2.75 ppm (H of 8 CH=); peak at 3.55 ppm (H of 8a CH=); peaks at 3.67 and 3.80 ppm (H of 2 CH=); peaks from 7.2 to 7.35 ppm (H of phenyl); peaks at 3.16 and 4.15 ppm (αH of phenyl); peaks from 2.2 to 3.0 ppm (other hydrogens).

STEP I: [4a SR trans]2,4,4a,5,6,7,8a,9-octahydro-5-benzyl-pyrazolo-[4,3-g]-1,4-benzoxazine 2.85 g of the product of Step H in 25 ml of ethanol were stirred for two hours under an inert atmosphere with 1 ml of hydrazine hydrate and after evaporating to dryness under reduced pressure, purifying by chromatography over silica (elution with methylene chloride-methanol 97-3), 2.2 g of [4a SR trans]2,4,4a,5,6,7,8a,9-octahydro-5-benzyl-pyrazolo-[4,3-g]-1,4-benzoxazine melting at 145° C. after crystallization from acetone were obtained.

Analysis: $C_{16}H_{19}N_3O$; Molecular weight=269.33. Calculated: %C 71.35; H% 7.11; %N 15.60; Found: %C 71.1; H% 7.2; %N 15.3.

EXAMPLE 2

[4a SR trans]-2,4,4a,5,6,7,8a,9-octahydro-pyrazolo-[4,3-g]-1,4-benzoxazine and its methane sulfonate 3.4 g of the product of Example 1 in 100 ml of methanol in the presence of 941 mg of 9.6% palladium on active carbon were hydrogenated to saturation. After filtering, rinsing with ethanol, evaporating the filtrate under reduced pressure, 2.13 g of [4a SR trans]-2,4,4a,5,6,7,8a,9-octahydro-pyrazolo-[4,3-g]-1,4-benzoxazine melting at ≈214° C. were obtained.

720 mg of the said base were dissolved in 10 ml of methanol and 0.26 ml of methane sulfonic acid were added. After crystallization and filtering and drying under reduced pressure, 776 mg of [4a SR trans]-2,4,4a,5,6,7,8a,9-octahydro pyrazolo-[4,3-g]-1,4-benzoxazine as its methane sulfonate melting at ≈262° C. were obtained.

Analysis: $C_{10}H_{16}N_3O_4S$; Molecular weight=275.328. Calculated: %C 43.62; %H 6.22; %N 15.26; %S 11.64; Found: %C 43.7; %H 6.3; %N 15.3; %S 11.6.

EXAMPLE 3

[4a SR trans]-5-propyl-2,4,4a,5,6,7,8a,9-octahydro-pyrazolo-[4,3-g]-1,4-benzoxazine and its oxalate A mixture of 1.14 g of the product of Example 2 in 10 ml of dimethylformamide was stirred for 2 hours at 60° C. with 0.63 ml of propyl iodide in the presence of 1.06 g of potassium carbonate. After cooling, adding water, extracting several times with methylene chloride, drying, evaporating to dryness under reduced pressure, purifying by chromatography over silica and eluention with methylene chloride-methanol (95-5), 1.08 g of [4a SR trans]-5-propyl-2,4,4a,5,6,7,8a,9-octahydro-pyrazolo-[4,5-g]-1,4-benzoxazine were obtained.

Formation of the oxalate

A solution of 488 mg of oxalic acid in 5 ml of methanol was added to a solution of 1.2 g of the said base in 10 ml of methanol and after crystallizing, filtering, washing with methanol and crystallizing from methanol, 1.04 g of [4a SR trans]-5-propyl-2,4,4a,5,6,7,8a,9-octahydro-pyrazolo-[4,5-g]-1,4-benzoxazine as its oxalate melting ≈220° C. were obtained.

Analysis: $C_{14}H_{21}N_3O_5$; molecular weight=311.33. Calculated: %C 54.01; %H 6.80; %N 13.49; Found: %C 54.1; %H 6.9; %N 13.6.

EXAMPLE 4

Hydrochloride of 4a RS (4aα,7α,8aβ)-7-methylthio-methyl-2,4,4a,5,6,7,8a,9-octahydro-5-propylpyrazolo-[3,4-g]-1,4-benzoxazine STEP A: Ethyl-[1RS-(1α,2β,4α)]-2-hydroxy-3-[[2-hydroxy-4-[(1,1-dimethyl ethyl)-dimethylsilyloxy]-cyclohexyl]-benzylamino]-propionate A mixture of 3.35 g of dimethyl(1,1-dimethylethyl)[[1RS-(1α,3β,4α)-3-hydroxy-4-[benzylamino]-cyclohexyl]-silane prepared as in Step C of Example 1, 30 ml of ethanol and 4.64 g of ethyl glycidate was stirred for 4 hours at reflux under nitrogen and after concentrating to dryness under reduced pressure, and purifying by chromatography over silica (eluent: benzene-ethyl acetate 7-3), 4.5 g of ethyl [1RS-(1α,2β,4α)]-2-hydroxy-3-[[2-hydroxy-4-[(1,1-dimethyl-ethyl)-dimethylsilyloxy]-cyclohexyl]-benzylamino]-propionate were obtained.

STEP B: Ethyl [2RS-(2α,4aα,7β,8aβ)-7-[dimethyl-(1,1-dimethylethyl)-silyloxy]-octahydro-4-benzyl-2H-1,4-benzoxazine-2-carboxylate 6.58 ml of tris dimethylaminophosphine were added dropwise to a mixture of 4.4 g of the product of Step A in 40 ml of methylene chloride and 4.5 g of N-chlorodiisopropylamine cooled to −40° C. and after stirring for 15 minutes at −40° C. and letting the temperature return to ambient, adding water, extracting with methylene chloride, drying and concentrating to dryness under reduced pressure, 8 g of crude product were obtained which was purified by chromatography over silica (eluent: benzene-ethyl acetate 9-1) to obtain a mixture of isomers of ethyl [2RS-(2α,4aα,7β,8aβ)-7-[dimethyl-(1,1-dimethylethyl)-silyloxy]-octahydro-4-benzyl-2H-1,4-benzoxazine-2-carboxylate at the level of the ethyl carboxylate (⅔ of equatorial CO₂Et and ⅓ of axial CO₂Et).

STEP C: Ethyl [2RS-(2α,4aα,7β,8aβ)]-7-hydroxy-octahydro-4-benzyl-2-H-1,4-benzoxazine-2-carboxylate A mixture of 65.5 g of the product of Step B in the form of a mixture of diastereoisomers in 300 ml of tetrahydrofuran and 380 ml of a molar solution of tetrabutylammonium fluoride in tetrahydrofuran was stirred for 16 hours at ambient temperature under an inert atmosphere. After pouring in water, extracting with methylene chloride, drying and concentrating to dryness under reduced pressure, 82 g of crude product were obtained which was purified by chromatography over silica (eluent: cyclohexane-ethyl acetate 5-5) to obtain 17.5 g of isomer A (equatorial CO₂Et) and 9.8 g of isomer B (axial CO₂Et) melting at 126°–128° C.

STEP D: Ethyl [2RS (2α,4aα,8aβ)]-7-oxo-octahydro-4-benzyl-2H-1,4-benzoxazine-2-carboxylate 51 g of N-chloro-succinimide in 1400 ml of toluene were cooled to 0° C. under nitrogen and 35.5 ml of dimethylsulfide were added dropwise. After cooling to −25° C., a solution of 24.3 g of the product of Step C in the form of a mixture of diastereoisomers in 250 ml of toluene was added dropwise over 30 minutes. The mixture was stirred for 2 hours at −25° C. and then over 10 minutes, 80 ml of triethylamine were added. After letting the temperature return to ambient, adding water, decanting, drying and concentrating to dryness under reduced pressure, 60 g of ethyl [2RS (2α,4aα,8aβ)]-7-oxo-octahydro-4-benzyl-2H-1,4-benzoxazine-2-carboxylate were obtained which was purified by chromatography over silica (eluent: cyclohexane-ethyl acetate 5-5) to obtain 13.9 g of isomer A (CO$_2$Et at α) melting at 104° C. and 5.4 g of isomer B (CO$_2$Et at β) melting at 102° C.

STEP E: 4a RS (4aα,7α,8aβ)-hydrazide of 2,4,4a,5,6,8a,9-octahydro-5-benzyl pyrazolo-[4,3-g]-1,4-benzoxazine-7-carboxylic acid 317 mg of ethyl 2RS (2α,4aα,8aβ)-7-oxo-octahydro-4-benzyl-2H-1,4-benzoxazine-2-carboxylate in 7.5 ml of toluene and 2.5 ml of dimethylformamide dimethylacetal were refluxed for 16 hours with stirring and after concentrating to dryness under reduced pressure, the residue was taken up in 4 ml of ethanol. 0.2 ml of hydrazine hydrate were added and the mixture was stirred for 12 hours at ambient temperature and after concentrating to dryness under reduced pressure and chromatographing over silica (eluent: methylene chloride-methanol 9-1), 234 mg of crude product melting at 165°–170° C. were obtained in the form of a mixture of the desired product and of 5a RS (5aα,8α,9aβ)-hydrazide of 2,4,5,5a,6,7,8,9a-octahydro-6-benzyl-pyrazolo-[3,4-H]-benzoxazine-8-carboxylic acid which was separated by a further chromatography over silica (eluent: methylene chloride-methanol 98-2).

STEP F: Methyl 4a-RS (4aα,7α,8β)-2,4,4a,5,6,7,8a,9-octahydro-5-benzyl-pyrazolo-[4,3-g]-benzoxazine-7-carboxylate A mixture of 327 mg of the product of Step E in 20 ml of methanol and 5 g of Amberlite resin was refluxed for 16 hours with stirring under nitrogen. The resin was filtered off with the product which was freed by a methanol-triethylamine mixture (2-1) and concentrated to dryness under reduced pressure to obtain 226 mg of methyl 4a RS (4aα,7α,8β)-2,4,4a,5,6,7,8a,9-octahydro-5-benzyl-pyrazolo-[4,3-g]-benzoxazine-7-carboxylate melting at 225° C.

STEP G: Methyl 4a-RS (4aα,7α,8aβ)-2,4,4a,5,6,7,8a,9-octahydro pyrazolo-[4,3-g]-1,4-benzoxazine-7-carboxylate A mixture of 1.44 g of the product of Step F in 50 ml of methanol in the presence of 380 mg of 95% palladium was hydrogenated for 4 hours. After filtering and concentrating to dryness under reduced pressure, 1.08 g of methyl 4a RS (4aα,7α,8aβ)-2,4,4a,5,6,7,8a,9-octahydro pyrazolo-[4,3-g]-1,4-benzoxazine-7-carboxylate melting at 188° C. were obtained.

STEP H: Methyl 4a RS (4aα,7α,8aβ)-2,4,4a,5,6,7,8a,9-octahydro-5-propyl-pyrazolo-[4,3-g]-1,4-benzoxazine-7-carboxylate A mixture of 850 mg of the product of Step G in 10 ml of dimethylformamide and 600 mg of potassium carbonate and 0.4 ml of propyl iodide was stirred for 2 hours at 60° C. under nitrogen. After diluting with water, extracting with methylene chloride, drying and concentrating to dryness under reduced pressure, 1 g of methyl 4a RS (4aα,7α,8aβ)-2,4,4a,5,6,7,8a,9-octahydro-5-propyl-pyrazolo-[4,3-g]-1,4-benzoxazine-7-carboxylate was obtained which was purified by chromatography over silica (eluent: methylene chloride-methanol 95-5).

STEP I: 4a-RS (4aα,7α,8aβ)-2,4,4a,5,6,7,8a,9-oxtahydro-5-propyl-pyrazolo-[4,3-g]-1,4-benzoxazine-7-methanol.

A mixture of 650 mg of the product of Step H in 10 ml of methanol and 5 ml of dioxane and 650 mg of sodium borohydride at 95% was refluxed for 90 minutes under nitrogen. After cooling, taking up in methylene chloride, washing with water, drying and concentrating to dryness under reduced pressure, 667 mg of 4a-RS (4aα,7α,8aβ)-2,4,4a,5,6,7,8a,9-octahydro-5-propyl-pyroazolo-[4,3-g]-1,4-benzoxazine-7-methanol were obtained which was purified by chromatography over silica (eluent: methylene chloride-methanol 9-1).

STEP J: 4a-RS (4aα,7α,8aβ)-2-[(4-methyl-phenyl)-sulfonyl]-2,4,4a,5,6,7,8a,9-octahydro-5-propylpyrazolo-[4,3-g]-1,4-benzoxazine-7-methanol and the corresponding isomer 1-[(4-methylphenyl)-sulfonyl]

380 mg of the product of Step I were mixed in 5 ml of pyridine under nitrogen and a solution of 575 mg of tosyl chloride in 5 ml of pyridine was added dropwise at ambient temperature. After stirring for 3 hours, diluting with water, extracting with methylene chloride, washing with water, drying and concentrating to dryness under reduced pressure, 680 mg of 4a-RS (4aα,7α,8aβ)-2-[(4methylphenyl)-sulfonyl]-2,4,4a,5,6,7,8a,9-octahydro-5-propylpyrazolo-[4,3-g]-1,4-benzoxazine-7methanol and the corresponding isomer 1-[(4-methylphenyl)-sulfonyl] were obtained which was purified by chromatography over silica (eluent: methylene chloride-methanol (95.5)). 550 mg of product were obtained which was crystallized from ether. It melted at 102°–105° C. in the form of a mixture of the 2-[(4-methylphenyl)-sulfonyl]-isomer and 1-[(4-methyl phenyl)-sulfonyl]-isomer.

STEP K: 4-methyl-benzene sulfonate of 4a-RS (4aα,7α,8aβ)-2-[(4-methylphenyl)-sulfonyl]-2,4,4a,5,6,7,8a,9-octahydro-5-propyl-pyrazolo-[4,3-g]-1,4-benzoxazine-7-methanol and the corresponding isomer 1-[(4-methylphenyl)-sulfonyl]

A solution of 440 mg of tosyl chloride in 5 ml of pyridine was added dropwise to a solution of 470 mg of the product of Step J in 5 ml of pyridine. After stirring for 5 hours at ambient temperature, diluting with water, extracting with methylene chloride, drying and concentrating to dryness under reduced pressure, 605 mg of 4-methyl-benzene sulfonate of 4a RS (4aα,7α,8aβ)-2-[(4-methylphenyl)-sulfonyl]-2,4,4a,5,6,7,8a,9-octahydro-5-propyl-pyrazolo-[4,3-g]-1,4-benzoxazine-7-methanol and the corresponding isomer 1-[(4-methylphenyl)-sulfonyl)] were obtained which was purified by chromatography over silica (eluent: methylene chloride-methanol 98-2) then chromatographed over silica (eluent: cyclohexane-ethyl acetate 5-5).

STEP L: 4a RS (4aα,7α,8aβ)-7-methylthiomethyl-2,4,4a,5,6,7,8a,9-octahydro-5-propylpyrazolo-[3,4-g]-1,4-benzoxazine hydrochloride 10 ml of dimethylacetamide and 900 mg of sodium hydride were added to 3 ml of methylmercaptan cooled to 0° C. and after allowing the temperature to return to ambient, a solution of 450 mg of product of Step K in the form of a mixture of isomers in 5 ml of dimethylacetamide was added dropwise. After stirring for 2 hours, pouring onto a mixture of water and ice, extracting with methylene chloride, washing with water, drying and concentrating to dryness under reduced pressure, 750 mg of crude desired product were obtained which was purified by chromatography on silica (eluent: methylene chloride-methanol 95-5).

0.5 ml of methanol solution of hydrochloric acid was added to 190 mg of the said base in solution in 3 ml of acetone and after crystallizing for 16 hours at +4° C., the crystals were separated, washed with several drops of acetone, dried at 80° C. under reduced pressure to obtain 210 mg of 4a RS (4aα,7α,8aβ)-7-methylthiomethyl-2,4,4a,5,6,7,8a,9-octahydro-5-propylpyrazolo-[3,4-g]-1,4-benzoxazine hydrochloride which was crystallized from methanol and melted at 160°-165° C.

Analysis: $C_{14}H_{28}N_3ClSO·1.6HCl·2.3H_2O$; molecular weight=381.16. Calculated: %C 44.11; %H 7.72; %N 11.02; %Cl 14.9; %S 8.41; Found: %C 44.2; %H 7.4; %N 10.7; %Cl 15.2 %S 8.3.

EXAMPLE 5

(±)-4a RS (4aα,7α,8aβ)-5-methyl-7-(methylthiomethyl)-2,4,4a,5,6,7,8a,9-octahydro pyrazolo-[4,3-g]-1,4-benzoxazine STEP A: 4a RS (4aα,7α,8aβ)-2,4,4a,5,6,7,8a,9-octahydro-5-methyl pyrazolo-[4,3-g]-1,4-benzoxazine-7-methanol 630 mg of product of Step G of Example 4 in 20 ml of methanol and 311 mg of soium cyanoborohydride and 0.25 ml of 37% formaldehyde were stirred under nitrogen for 90 minutes at ambient temperature. 10 ml of dioxane and 630 mg of 95% sodium borohydride were added and the mixture was refluxed for 1 hour. After cooling, diluting with water, concentrating to dryness under reduced pressure and chromatography over silica (eluent: methylene chloride-methanol 9-1 at 0.5% triethylamine), 302 mg of 4a RS (4aα,7α,8aβ)-2,4,4a,5,6,7,8a,9-octahydro-5-methyl-pyrazolo-[4,3-g]-1,4-benzoxazine-7-methanol melting at 210° C. owere obtained.

STEP B: 4a RS (4aα,7α,8aβ)-2-[4-methylphenyl-sulfonyl]-2,4,4a,5,6,7,8a,9-octahydro-5-methylpyrazolo-[4,3-g]-1,4-benzoxazine-7-methanol and the corresponding 1-[(4-methylphenyl)-sulfonyl] isomer Using the procedure of Step J of Example 4, 282 mg of the product of Step A were reacted to obtain 536 mg of crude product which was purified by chromatography over silica (eluent: methylene chloride-methanol 9-1) to obtain 230 mg of 4a RS (4aα,7α,8aβ)-2-[4-methyl phenyl-sulfonyl]-2,4,4a,5,6,7,8a, 9-octahydro-5-methyl pyrazolo-[4,3,-g]-1,4-benoxazine-7-methanol and the corresponding 1-[(4-methylphenyl)-sulfonyl]-isomer melting at 194° C.

STEP C: 4-methylbenzene sulfonate of 4a RS (4aα,7α,8aβ)of 2-[(4-methylphenyl)-sulfonyl]-2,4,4a,5,6,7,8a,9-octahydro-5-methyl pyrazolo-[4,3-g]-1,4-benzoxazine-7-methanol and the corresponding 1-[(4-methylphenyl)-sulfonyl]]

Using the procedure of Stpe K of Example 4, 265 mg of the product of Step B were reacted to obtain 390 mg of crude product which was purified by chromatography over silica (eluent: methylene chloride at 1.5% of methanol) to obtain 180 mg in the form of a mixture of isomers of 4-methylbenzene sulfonate of 4a RS (4aα,7α,8aβ) of 2-[4-methylphenyl)-sulfonyl]-2,4,4a,5,6,7,8a,9-octahydro-5-methyl pyrazolo-[4,3-g]-1,4-benzoxazine-7-methanol and the corresponding 1-[(4-methylphenyl)-sulfonyl].

STEP D: (±)-4a-RS (4aα,7α,8aβ)-5-methyl-7-(methylthio methyl)-2,4,4a,5,6,7,8a,9-octahydropyrazolo-[4,3-g]-1,4-benzoxazine Using the procedure of Step L of Example 4, 170 mg of the product of Step C were reacted to obtain 220 mg of crude product which was purified by chromatography over silica (eluent: methylene chloride-methanol 95-5). 75 mg of product were collected which was dissolved in methylene chloride, filtered and concentrated to dryness under reduced pressure and the residue was taken up in ether and methylene chloride. The crystallized product was separated and dried at 50° C. under reduced pressure to obtain (±) 4a RS (4aα,7α,8aβ)-5-methyl-7-(methylthio methyl)-2,4,4a,5,6,7,8a,9-octahydropyrazolo-[4,3-g]-1,4-benzoxazine melting at 147° C.

Analysis: $C_{12}H_{18}N_3SO$; molecular weight=253.34. Calculated: %C 56.89; %H 7.56; %N 16.58; %S 12.65; Found: %C 56.9; %H 7.8; %N 16.2; %S 12.65.

EXAMPLE 6

Tablets were prepared containing 10 mg of [4a SR trans]-2,4,4a,5,6,7,8a,9-octahydropyrazolo-[4,3-g]-1,4-benzoxazine methane sulfonate and sufficient excipient of lactose, starch, talc, and magnesium stearate for a tablet weight of 100 mg.

EXAMPLE 7

Tablets were prepared containing 5 mg of [4a SR trans]-5-propyl-2,4,4a,5,6,7,8a,9-octahydropyrazolo-[4,3-g]-1,4-benzoxazine oxalate and sufficient excipient of lactose, starch, talc and magnesium stearate for a tablet of 100 mg.

PHARMACOLOGICAL STUDY

A. Rotation behavior after unilateral lesion of the nigra-striated bundle by 6-hydroxydopamine Male rats of 220 g were injured in the nigra-striated dopaminergic bundle according to Ungerstedt's method [Ungerstedt, Acta physiol. Scand. (1971) Vol. 82, suppl. 367.69–93], modified by unilateral injection of 9.2 μg of 6-hydroxydopamine hydrochloride in solution in 4 μl of physiological solution containing 0.5 mg/ml of ascorbic acid. The test products were administered by intraperitoneal route and the animals treated in groups of 8 were placed individually in a rotometer which allowed the counting of the number of rotations carried out by each animal in the opposite direction to the injured side under the test conditions The product of Example 3 caused rotations contra-lateral to the injured side starting at a dose of 0.05 mg/kg. It therefore caused an agonistic action on the dopaminergic receptors at the central level.

B. Stereotype behavior

The tests were carried out on groups of 5 male rats weighing 150 to 180 g and each animal was placed individually in a barred cage (29×25×17 cm) containing a few wood shaving. The test product was administered intraperitoneally and the behavior of the animals was noted every half hour over 5 hours with the rating recommended by HALLIWELL et al. [Brit. J. Pharmacol. (1964), Vol. 23, p. 330–350]. The animal was asleep (0), it was awake but immobile (1), it turned in the cage (2), it sniffed the cover (3), it licked the walls (4), it touched the wood shavings or the bars of the cage with its teeth (5), it bit the shavings or the bars of the cage (6).

The total is determined of the scores per group taken at different times after administrationof the product studied. Starting at a dose of 0.1 mg/kg, the product of Example 3 caused stereotype movements and it therefore had a dopaminergic agonist effect at the central level.

C. Determination of hypotensive activity

The hypotensive activity was studied on male rats of WISTAR strain weighing about 300 g and anesthetised with nembutal (50 mg/kg by intraperitoneal route). The test product was administered intravenously into the jugular vein and the carotidien arterial pressure was measured before and after administration of the product. The following table reports the variations expressed in percentages of the arterial pressure after administration of the product in relation to the initial control arterial pressure.

| Product of Example | Dose in mg/kg | % Variation of arterial pressure | |
|---|---|---|---|
| | | 5 minutes after administration | 30 minutes after administration |
| 3 | 0.1 | −26 | −21 |
| | 0.01 | −19 | −8 |
| 4 | 0.1 | −21 | −17 |
| | 0.01 | −5 | −5 |

Bradycardia was also be noted. These hypotensive and bradycardiac effects are blocked by sulpiride and they are therefore of dopaminergic origin.

D. Determination of antihypertensive activity

The anithypertensive activity was studied on spontaneously hypertensive male rats of the OKAMOTO strain aged 20 weeks and weighing 300 to 320 g. The product was administered orally 48 hours after the positioning of an intracarotidien catheter to measure the arterial pressure. The pressure was measured before and 1 hour after administration of the product. For the product of Example 3, at a dose of 0.5 mg/kg the variation in percentage of arterial pressure after administration of the product in relation to the initial control pressure was −15% one hour after administration.

E. Antianoxic activity

A—Test of hypobare anoxemia:

Male mice weighing 20–22 g, having fasted for 5 hours, were divided into groups of 10 animals and the test product was administered to the animals subcutaneously. Fifteen minutes after administration of the product, the animals were placed in a 2 liter dessicator in which the pressure was brought rapidly to 90 mm of Hg by a pump, and their time of survival was noted expressed in seconds. The increase of the survival time was recorded expressed as a percentage of the animals treated in relation to the control animals submitted to the same conditions. The following results were obtained.

| Product of Example | Doses in mg/kg orally | Increase in survival time |
|---|---|---|
| 3 | 0.1 | +90% |
| | 0.01 | +37% |
| 4 | 1 | +32% |

B - enolase test

Suffering cerebral neuronal cells release enolase and the test was carried out on rats whose brain had been totally deprived of blood by ligature of the arteries supplying the brain. The product of Example 3 administered intraperitoneally diminished the releasing of enolase to a dose of 0.1 mg/kg. Therefore it was considered that it protected the cerebral cells against ischemia.

F. Acute toxicity

The lethal dose $LD_0$ of the product of Example 3 was evaluated after oral administration to mice. $LD_0$ is the maximum dose not causing any mortality in 8 days. The product had a $LD_0$ of $\geq 200$ mg/kg.

Various modifications of the products and metods of the invention may be made without departing from the spirit or scope thereof and it is to be understood that the invention is intended to be limited only as defined in the appended claims.

What is claimed is:

1. A method of treating cerebral senescence and cerebral hypoxia in warm-blooded animals comprising administering to warm-blooded animals an antianoxically effective amount of at least one compound of the formula

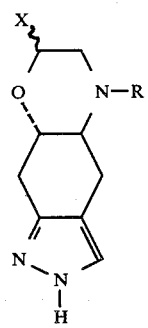

I wherein R is selected from the group consisting of hydroge, alkyl of 1 to 5 carbon atoms, cycloalkylalkyl of 4 to 7 carbon atoms, alkenyl and alkynyl of 3 to 5 carbon atoms with the proviso that the multiple bond is not between the carbon α- and β- to the nitrogen atom, aralkyl of 7 to 12 carbon atoms and aralkyl of 7 to 12 carbon atoms substituted with at least one member of the group consisting of alkyl and alkoxy of 1 to 5 carbon atoms, amino, —OH and halogen, X is selected from the group consisting of hydrogen and —CH2—S—Alk, Alk is alkyl of 1 to 5 carbon atoms, the wavy line indicates the α- or β-position and their non-toxic, pharmaceutically acceptable acid addition salts.

2. A method of claim 1 wherein X is hydrogen.

3. A method of claim 1 wherein X is —CH$_2$—S—Alk.

4. A method of claim 1 wherein X is —CH$_2$—S—CH$_3$.

5. A method of claim 1 wherein R is hydrogen or alkyl of 1 to 5 carbon atoms.

6. A method of claim 2 selected from the group consisting of [4a SR trans]-5-propyl-2,4,4a,5,6,7,8a,9-octahydropyrazolo-[4,3-g]-1,4-benzoxazine and its non-toxic pharmaceutically acceptable acid addition salts.

* * * * *

UNITED STATES PATENT AND TRADEMARK OFFICE
CERTIFICATE OF CORRECTION

PATENT NO. : 4,661,482  
DATED : April 28, 1987  
INVENTOR(S) : Lucien Nedelec et al.

It is certified that error appears in the above-identified patent and that said Letters Patent is hereby corrected as shown below:

| Col. | Line | Abstract | | |
|---|---|---|---|---|
| [57] | | 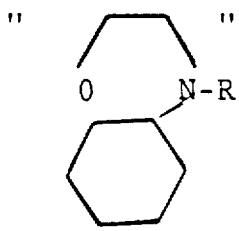 | should be | 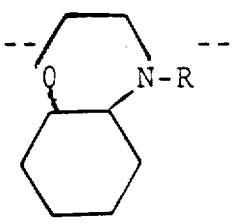 |
| 2 | 5&6 | "-CH-$_2$" | should be | -- -CH$_2$-- |
| 4 | 6 | "R$_1$-CH-R$_2$" | should be | --R$_1$-CH-R$_2$-- |
| 4 | 35 |  | should be | 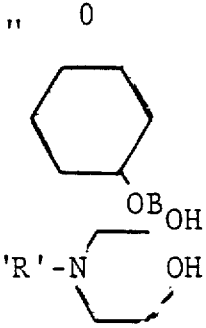 |
| 5 | 5 | 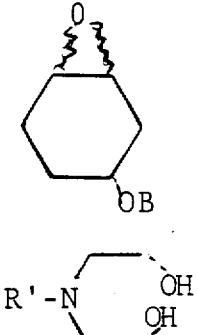 | should be | 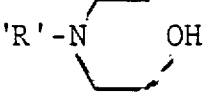 |
| 8 | 24&25 | "Alk$_2$" | should be | --Alk$_2$-- |

UNITED STATES PATENT AND TRADEMARK OFFICE
CERTIFICATE OF CORRECTION

PATENT NO. : 4,661,482  Page 2 of 3
DATED : April 28, 1987
INVENTOR(S) : Lucien Nedelec et al.

It is certified that error appears in the above-identified patent and that said Letters Patent is hereby corrected as shown below:

| Col. | Line | | | | |
|---|---|---|---|---|---|
| 9 | 15 | " R'-N⟨COOAlk₁ | should be | -- R'N⟨COOAlk | |
| 9 | 30 | " " " " " " " " " " " " " " " " | | | |
| 11 | 37&38 | "[1 SR" | should be | --[1 SR-- | |
| 11 | 51 | "≈65°C" | " " | -- ≈65°C-- | |
| 13 | 53 | "10 ml" | " " | --10 ml-- | |
| 13 | 54 | "60°C" | " " | --60°C-- | |

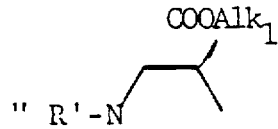

UNITED STATES PATENT AND TRADEMARK OFFICE
CERTIFICATE OF CORRECTION

PATENT NO. : 4,661,482  
DATED : April 28, 1987  
INVENTOR(S) : Lucien Nedelec et al.

Page 3 of 3

It is certified that error appears in the above-identified patent and that said Letters Patent is hereby corrected as shown below:

| Col. | Line | | |
|---|---|---|---|
| 13 | 55 | "1.06 g" should be | --1.06 g-- |
| 16 | 5 | "10, ml" should be | --10 ml-- |
| 17 | 31 | "HC12.3H" should be | --HCl 2.3H-- |
| 17 | 58 | "2,4,4a,5,6,7-," should be | 2,4,4a,5,6,7,-- |
| 18 | 10 | "Stpe K" should be | --Step K-- |
| 18 | 16&17 | "2,4,4a,5,6,7-," should be | 2,4,4a,5,6,7,--- |
| 20 | 37 | "$\geqslant 200$ mg/kg" should be | --$\geqslant 200$ mg/kg-- |
| 22 | 4 | "--$CH_2$--" should be | --$CH_2$-- |

Signed and Sealed this

Twenty-fifth Day of August, 1987

Attest:

DONALD J. QUIGG

Attesting Officer  Commissioner of Patents and Trademarks